(12) United States Patent
Aymard et al.

(10) Patent No.: US 9,605,282 B2
(45) Date of Patent: Mar. 28, 2017

(54) METHOD FOR PRODUCING ALCOHOLS AND/OR SOLVENTS FROM LIGNOCELLULOSIC BIOMASS WITH WASHING OF THE SOLID RESIDUE OBTAINED AFTER FERMENTATION

(71) Applicant: IFP ENERGIES NOUVELLES, Rueil-Malmaison (FR)

(72) Inventors: Caroline Aymard, Lyons (FR); Pierre-Antoine Bouillon, Bron (FR); Stephanie Fleurier, Lyons (FR); Sylvain Louret, Lyons (FR); Larissa Perotta, Lyons (FR); Eszter Toth, Lyons (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 0 days.

(21) Appl. No.: 14/772,911

(22) PCT Filed: Feb. 6, 2014

(86) PCT No.: PCT/FR2014/050223
§ 371 (c)(1),
(2) Date: Sep. 4, 2015

(87) PCT Pub. No.: WO2014/135755
PCT Pub. Date: Sep. 12, 2014

(65) Prior Publication Data
US 2016/0017380 A1    Jan. 21, 2016

(30) Foreign Application Priority Data
Mar. 6, 2013 (FR) .................. 13 51989

(51) Int. Cl.
*C12P 7/14* (2006.01)
*C12P 7/10* (2006.01)

(52) U.S. Cl.
CPC ........ *C12P 7/14* (2013.01); *C12P 7/10* (2013.01); *C12P 2201/00* (2013.01); *C12P 2203/00* (2013.01); *Y02E 50/16* (2013.01)

(58) Field of Classification Search
None
See application file for complete search history.

(56) References Cited

U.S. PATENT DOCUMENTS

| 7,465,791 B1 | 12/2008 | Hallberg et al. |
| 8,110,383 B2 | 2/2012 | Jonsson et al. |
| 8,227,004 B2 | 7/2012 | Hallberg et al. |
| 8,528,463 B2 | 9/2013 | Hallberg et al. |
| 8,980,599 B2 | 3/2015 | Tolan et al. |
| 2008/0295980 A1 | 12/2008 | Hallberg et al. |
| 2008/0299629 A1* | 12/2008 | Hallberg ........ B01D 3/002 435/161 |
| 2009/0035826 A1 | 2/2009 | Tolan et al. |
| 2009/0117226 A1 | 5/2009 | Hallberg et al. |
| 2011/0217746 A1 | 9/2011 | Jonsson et al. |
| 2012/0100585 A1 | 4/2012 | Ropars et al. |
| 2012/0289685 A1 | 11/2012 | Hallberg et al. |
| 2014/0045237 A1 | 2/2014 | Galvao et al. |

FOREIGN PATENT DOCUMENTS

| EP | 2169074 A1 | 3/2010 |
| WO | 2009015481 A1 | 2/2009 |
| WO | 2010130888 A2 | 11/2010 |
| WO | 2012129622 A1 | 10/2012 |

OTHER PUBLICATIONS

International Search Report and Search Opinion from PCT/FR2014/050223 dated Apr. 2, 2014.
Eva Palmqvist et al. "Simultaneous detoxification and enzyme production of hemicellulose hydrolysates obtained after steam pretreatment" Enzyme and Microbial Technology, (1997), vol. 20, pp. 286-293.

* cited by examiner

*Primary Examiner* — Suzanne M Noakes
*Assistant Examiner* — Stephen Chong
(74) *Attorney, Agent, or Firm* — Millen White Zelano and Branigan, PC; Csaba Henter; John Sopp

(57) ABSTRACT

The process for the production of alcohol and/or solvent from a biomass feedstock comprises the stages for pretreatment (P) of the biomass feedstock, for enzymatic hydrolysis (H1 and HF), and for fermenting the hydrolyzate (HF). To prevent solids from being sent and to facilitate operating the section for purifying the fermentation products, at least a portion of the solid material in the fermentation wine is extracted (Ex1) to obtain a stream of solid residue (11) comprising lignin and a fermentation wine (12) that is low in solid material. Then, the stream of solid residue is washed (L) with a liquid stream to recover a liquid stream that is enriched with fermentation products (16). The liquid stream that is enriched with fermentation products (16) is recycled in the enzymatic hydrolysis stage (H1) to recover any fermentation product and to increase the overall yield of the process.

11 Claims, 3 Drawing Sheets

METHOD FOR PRODUCING ALCOHOLS AND/OR SOLVENTS FROM LIGNOCELLULOSIC BIOMASS WITH WASHING OF THE SOLID RESIDUE OBTAINED AFTER FERMENTATION

This invention is part of the framework of a process for the production of so-called "second-generation" alcohols and/or solvents from lignocellulosic biomass. It relates more particularly to a process for the production of ethanol and/or solvents.

The lignocellulosic biomass represents one of the most abundant renewable resources on earth. The substrates being considered are very varied since they relate at the same time to ligneous substrates (leafy and resinous), the by-products of agriculture (straw), or those of the industries that generate lignocellulosic waste (farm-produce industries, paper mills).

The lignocellulosic biomass consists of three primary polymers: cellulose (35 to 50%), which is a polysaccharide that essentially consists of hexoses; hemicellulose (20 to 30%), which is a polysaccharide that essentially consists of pentoses; and lignin (15 to 25%), which is a polymer with a complex structure and high molecular weight, composed of aromatic alcohols connected by ether bonds. These different molecules are responsible for the inherent properties of the plant wall and are organized in a complex intertwining.

The process for biochemical transformation of lignocellulosic materials into ethanol in general comprises a stage for physico-chemical pretreatment, followed by a stage for enzymatic hydrolysis using an enzymatic cocktail, a stage for ethanolic fermentation of released sugars, and a stage for purification of the fermentation products. Under certain configurations of the process scheme, the stages of enzymatic hydrolysis and fermentation may take place in the same reactor, in a fermentation configuration called SSF (Simultaneous Saccharification and Fermentation). The scheme that presents these two separate stages of the process is a scheme of the SHF (Separated Hydrolysis and Fermentation) type. Examples are provided by the document "*Ethanol from Lignocellulosics: A Review of the Economy,*" M. von Silvers and G. Zacchi, Bioresource Technology 56 (1996) 131-140.

Among the three base polymers that comprise the lignocellulosic biomass, the cellulose and the hemicellulose are those that can most easily be upgraded into fermentation products. The lignin remains inert in the vast majority of the processes. This is why it is advantageous for the processes for the production of alcohol and solvent to separate the lignin from the reaction mixtures as soon as possible so as to reduce the size of the units and the costs of treatment and investment. The lignin can be separated at different stages of the process, for example in the pretreatment, between the stages for enzymatic hydrolysis and fermentation, if the process is in an SHF-type configuration, or in the stage for purification of the fermentation products.

The document "*Fuel Ethanol Production: Process Design Trends and Integration Opportunities,*" C. A. Cardona and O. J. Sanchez, Bioresource Technology 98 (2007) 2415-2457, describes a process where the lignin is solubilized in the presence of a solvent that makes it possible to separate the lignin from the cellulose and the hemicellulose, with the lignin next being precipitated during the pretreatment of the biomass. This solution prevents the presence of inert solids in the process starting from the enzymatic hydrolysis stage, but it has high operating costs. In addition, this configuration of the process does not promote a possible co-fermentation of the cellulosic and hemicellulosic sugars recovered in the pretreatment, considering that two streams having distinct properties and compositions are obtained.

Several processes describe the separation of the lignin between the stages for enzymatic hydrolysis and fermentation. The document "*A Techno-Economical Comparison of Three Processes for the Production of Ethanol from Pine,*" M. von Silvers and G. Zacchi, Bioresource Technology 51 (1995) 46-52, describes the impact of the washing of the recovered solid in terms of cost of the fermentation equipment, as well as a drop in the ethanol titer obtained at the end of fermentation. One advantage linked to this production method is the reduction in the size of the reactors owing to the elimination of inert solids and the subsequent possibility of separation and recycling of microorganisms used in the fermentation to the fermentation reactors.

Nevertheless, the SSF production method is often described as being the most advantageous in terms of overall yield. The enzymatic hydrolysis stage by itself is often hampered by the high sugar concentration in the medium at the end of the reaction, considering that sugars have an inhibiting effect on the activity of the enzymes. In an SSF-type process configuration, the fermentation microorganisms consume the available sugar in the medium, whereas at the same time, the sugar is produced by solubilization of cellulose by the enzymes. The sugar concentration in the reactor is thus always minimal, and the yield of the two reactions is maximal.

Process schemes based on the SSF not having solubilized the lignin in the pretreatment stage are configured for separating the lignin before the stage for purification of the fermentation products so as to prevent solids from being sent into the distillation columns downstream from the process ("*Ethanol from Lignocellulosic Biomass: Technology, Economics, and Opportunities,*" C. E. Wyman, Bioresource Technology 50 (1994) 3-16).

However, this separation is generally carried out by tools for physical separation, which exhibit the disadvantage that the recovered solid material can also contain trapped fermentation products. In this case, it is possible to add a stage for washing solids to the process, with the effluent from this washing stage being sent to the stage for purification of the fermentation products with the clarified fermentation wine. This represents a compromise between the recovery of fermentation products and the limitations provided by the energy penalty linked to the dilution of the wine to be distilled.

This invention proposes carrying out the separation of lignin and other optional inert solids after the fermentation stage. The solid material that consists primarily of lignin is next subjected to a washing cycle for recovering the trapped fermentation products, in particular the alcohols and the solvents. The washing liquid is next recycled in the enzymatic hydrolysis unit, which can be the same unit as the fermentation unit or which can be separate from the fermentation unit so as not to provide dilution to the existing streams.

In a general manner, the invention has as its object a process for the production of alcohol and/or solvent from a biomass feedstock, in which the following stages are carried out:

a) A pretreatment stage is carried out by heating and bringing the biomass feedstock into contact with water and an acid or base compound in such a way as to obtain a pretreated substrate, b) The pretreated substrate is brought into contact with cellulase enzymes and with a liquid stream that is enriched with fermentation products and obtained in stage e) in such a way as to obtain a hydrolyzate comprising a solid residue and a liquid phase containing sugars, c) An alcoholic fermentation of the hydrolyzate by means of an alcohologenic microorganism is carried out in such a way as to produce a fermentation wine comprising a solid material and a liquid phase containing fermentation products, d) At least a portion of the solid material contained in the fermentation wine is extracted in such a way as to obtain a stream that is enriched with solid material and a fermentation wine that is low in solid material, e) The stream that is enriched with solid material is washed with a liquid stream in such a way as to obtain said liquid stream that is enriched with fermentation products, with the liquid stream that is enriched with fermentation products being recycled in stage b), f) A stage for separation of the fermentation wine that is low in solid material is carried out in such a way as to obtain at least one purified stream comprising an alcohol or a solvent and at least one vinasse stream.

According to the invention, the liquid stream from stage e) can consist of fresh water. The liquid stream from stage e) can comprise at least a portion of the vinasse stream obtained in stage f).

In stage b), the liquid stream that is enriched with fermentation products can have a flow rate of between 50% and 1,500% by weight of the flow rate of pretreated substrate.

In stage e), it is possible to bring the stream that is enriched with solid material into contact with said liquid stream, and then it is possible to separate the liquid stream from the solid material.

It is possible to carry out stage d) in such a way that said stream that is enriched with solid material comprises between 15% by weight and 55% by weight of solid material and in such a way that said fermentation wine that is low in solid material comprises less than 15% by weight of solid material.

It is possible to carry out stage b) in a first reactor, and it is possible to carry out stage c) in a second reactor that is separate from the first reactor. Alternately, it is possible to carry out stage b) and stage c) simultaneously in the same reactor.

The cellulase enzymes can be produced by a microorganism that is selected from among the mushrooms that belong to the genera *Trichoderma, Aspergillus, Penicillium*, or *Schizophyllum*, or the anaerobic bacteria that belong to the genus *Clostridium*.

The alcohologenic microorganism can be selected from among the microorganisms of the genus *Saccharomyces, Saccharomyces cerevisiae, Schizosaccharomyces pombe, Saccharomyces uvarum, Saccharomyces diastaticus, Kluyveromyces fragilis, Candida shehatae, Pichia stipitis, Pachysolen tannophilis, Zymomonas mobilis, Clostridium, Escherichia coli*.

The biomass feedstock can consist of at least one of the following elements: wood, cultivated plants, agricultural lignocellulosic waste, residues of the industry for transformation of lignocellulosic materials.

In stage a), it is possible to carry out a vapor explosion of the biomass by exerting compression and then carrying out pressure relief of the biomass mixed with water and an acid compound.

In stage e), it is possible to use an alcohologenic organism that produces at least ethanol.

BRIEF DESCRIPTION OF THE FIGURES

Other characteristics and advantages of the invention will be better understood and will appear clearly from reading the description given below by referring to the drawings among which.

In terms of this invention, the solid and soluble compounds contained in a stream are referred to by the term "dry material," and the level of dry material of a stream is determined according to the ASTM E1756-01 method, which consists of a loss of mass at 105° C. The solid compounds that are present in a stream, with these solid compounds being insoluble in the liquid phase, are referred to by the term "solid material." The solid material can consist of lignin, hemicellulose and/or cellulose. The level of solid material contained in a stream can be determined by successive washing cycles of the stream with water and the analysis of the content of residual dry material of the washed stream.

Figure 1:
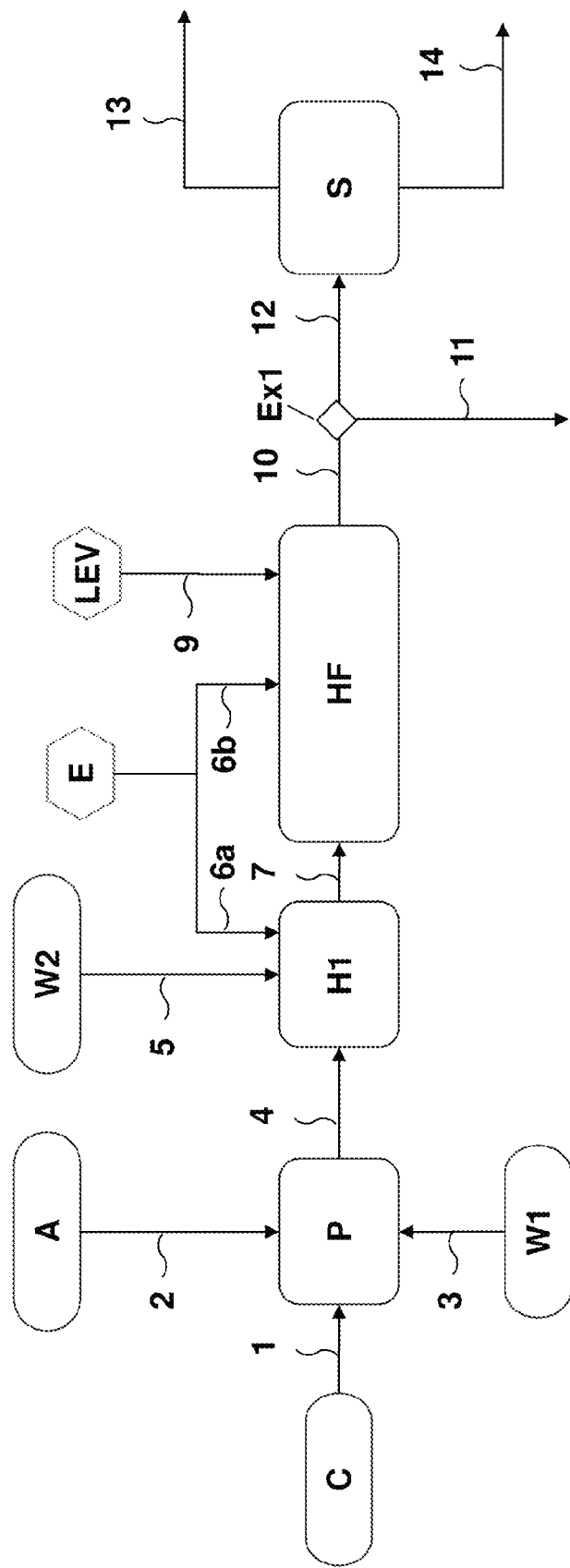
FIG. 1 is a diagrammatic depiction of an embodiment that is not in accordance with the invention.

With reference to FIG. 1, a biomass feedstock C is brought into the pretreatment unit P by means of the pipe 1. The biomass feedstock can consist of wood, straw, or corn stalks, products of dedicated forestry crops (for example, resinous crops such as spruce or pine, or leafy crops such as *eucalyptus*), plants of dedicated crops such as *Miscanthus* or switchgrass, residues of alcohologenic plants, sugar-producing plants (for example, sugar cane or beets) and grains (for example, corn, wheat, . . . ), products and residues of the papermaking industry, and products for transformation of lignocellulosic materials. The feedstock can consist of approximately 35 to 50% by weight of cellulose, 20 to 30% by weight of hemicellulose, and 15 to 25% by weight of lignin.

The necessary acid or base compound A and water W1 are respectively brought into the pretreatment unit P by means of the pipes 2 and 3 so as to carry out therein a hydrolysis reaction in an acid or base medium. In the unit P, the biomass feedstock C is brought into contact and mixed with water W1 and the compound A in a reactor. The pretreatment unit P can carry out a mechanical action, created, for example, by means of a two-screw-type extruder or a defibering unit.

Among the acid compounds, the compound A can be selected from among sulfuric acid, hydrochloric acid, nitric acid, acetic acid, or formic acid. Among the base compounds, the compound A can be selected from among potassium hydroxide, sodium hydroxide, and ammonia.

During the pretreatment stage in the unit P, at least one stage for heating the mixture of biomass C, water W1, and the compound A is carried out in a reactor. The water W1 can be introduced in vapor form. The pretreatment role is to make the cellulose accessible to enzymes by destructuring the lignocellulosic matrix. During pretreatment, preferably the hemicellulose is attacked, which for the most part is dissolved in the liquid phase.

According to a first embodiment, an alkaline pretreatment is carried out in the unit P. For example, in the unit P, it is possible to carry out a pretreatment with sodium sulfate, also called the Kraft process, conventionally used in the processes for production of papermaking products, called Kraft or "sulfate paste," at the end of which papermaking pastes are obtained. The alkaline chemical pretreatment carried out in the unit P can also be a pretreatment by explosion of the fibers with ammonia, also called AFEX (Ammonia Fiber Explosion) pretreatment, or pretreatment by percolation using ammonia with recycling, also called ARP (Ammonia Recycle Percolation) pretreatment.

The process with sodium sulfate or the Kraft process is based on the use of soda and sodium sulfate. The chemical treatment of the wood chips is done at 150-175° C. for a period of 1 to 7 hours based on the substrate that is used. The Kraft papermaking pastes are produced from the most varied biomasses but more particularly from the resinous arborescent types (softwood such as spruce or pine) or leafy arborescent types (hardwood such as *eucalyptus*) or else agricultural lignocellulosic waste (wheat straw, rice, etc.). They are partially delignified by means of high-temperature baking and in the presence of soda. This delignification is controlled by the operating parameters of the reactors. The baking is done in a vertical reactor, where the chips drop by gravity and meet the various baking liquors. The sodium sulfide is prepared directly from sodium sulfate by combustion. During baking, the sodium sulfide is hydrolyzed with soda, NaHS, and $H_2S$. The different sulfur-containing compounds that are present react with lignin to provide thio-lignins that are more easily soluble. The liquor applied to the chips is called white liquor. The liquor extracted from the reactor or digester containing the compounds eliminated from the wall is called black liquor. At the end of this alkaline pretreatment, the result is the production of a pretreated substrate, enriched with cellulose since it contains between 60 and 90% cellulose and between 5 and 20% hemicellulose.

The ARP (Ammonia Recycle Percolation) process is a pretreatment process using ammonia with recycling. This type of process is described in particular by Kim et al., 2003, Biores. Technol. 90 (2003), pp. 39-47. The high temperature of the percolation leads to a partial solubilization of both lignin and hemicelluloses; this solution is next heated for recycling ammonia and for recovering, on the one hand, the extracted lignin, for example for an energy upgrade, and, on the other hand, soluble sugars coming from hemicelluloses.

The AFEX (Ammonia Fiber Explosion) process consists in introducing the lignocellulosic substrate into a high-pressure cooker in the presence of ammonia and then causing an explosive pressure relief at the outlet of the reactor and recycling ammonia that is then in gaseous form. This type of process is described in particular by Teymouri et al., 2005, *Biores. Technol.* 96 (2005), pp. 2014-2018. This process primarily leads to a destructuring of the matrix of the biomass, but there is no phase separation of the lignin, hemicellulose, and cellulose compounds at the treatment outlet.

According to a second embodiment, an acid pretreatment is carried out in the unit P. For example, in the unit P, it is possible to carry out a baking-type pretreatment with dilute acid. In this embodiment, the biomass is brought into contact with a strong acid that is diluted in water, for example sulfuric acid, by using the biomass at low contents of dry materials, generally between 5 and 20% dry material. The biomass, acid, and water are brought into contact in a reactor and raised in temperature, generally between 120° C. and 200° C. During this process, the hemicellulosic compounds are primarily hydrolyzed into sugars, making it possible to destructure the lignocellulosic matrix. At the end of this acid pretreatment, the result is the production of a solid pretreated substrate, enriched with cellulose and lignin, as well as a liquid fraction that is enriched with sugars.

According to a third embodiment, it is also possible to carry out the process called "vapor explosion," or "SteamEx" or "steam explosion" according to English terminology, in the unit P. This is a process in which the lignocellulosic biomass is brought into contact with water in a reactor with a short dwell time, generally between 2 and 15 minutes, and at moderate temperatures, generally between 120° C. and 250° C., and at a pressure of between 5 and 50 bar. Water can be supplemented with an acid compound, for example sulfuric acid, or a base compound. At the outlet of the reactor, the biomass is expanded, for example to atmospheric pressure, in a gas/solid separator receptacle so as to produce a pretreated biomass with a high level of dry material, generally between 20 and 70% dry material.

The unit P can comprise additional stages, for example for setting the pH, which have as their object to facilitate the implementation and the effectiveness of the stages for enzymatic hydrolysis and fermentation.

A pretreated substrate is evacuated from the unit P via the pipe 4. The pretreated substrate consists of sugars dissolved in the liquid phase and solid material composed of lignin, cellulose, and hemicellulose, which has not been liquefied in the pretreatment P. The stream of pretreated substrate circulating in the pipe 4 preferably contains between 10% by weight and 60% by weight of dry material and even more preferably between 20% by weight and 55% by weight of dry material. A pretreated substrate is evacuated from the unit P via the pipe 4 into the unit H1.

The pretreated substrate is introduced into a reactor of the unit H1 for undergoing a first enzymatic hydrolysis stage called "liquefaction." Water W2 and enzymes E are respectively added into the unit H by means of the pipes 5 and 6*a* so as to carry out a reaction for enzymatic hydrolysis of the pretreated substrate. The quantities of pretreated substrate, water, and enzymes are adjusted in the stage in the unit H1 in such a way that the reaction medium comprises a solid material content that is generally between 5% and 40% by weight, preferably between 10% and 25% by weight. The liquefaction is preferably carried out at a pH of between 4 and 5.5 and at a temperature of between 40° C. and 60° C. The enzymes E can be produced by a microorganism, for examples mushrooms belonging to the genera *Trichoderma, Aspergillus, Penicillium* or *Schizophyllum*, or the anaerobic bacteria that belong to, for example, the genus *Clostridium*. The enzymes that are produced by these microorganisms contain in particular the cellulases and, optionally, hemicellulases, suitable for the intense hydrolysis of the cellulose and, optionally, hemicelluloses. In the unit H1, the conditions of the enzymatic hydrolysis, primarily the level of dry material of the mixture to be hydrolyzed and the quantity of enzymes used, are selected in such a way that a solubilization of the cellulose of between 10% and 40% by weight, preferably between 20% and 40% by weight, is obtained relative to the total weight of the cellulose contained in the pretreated substrate. A substrate that is liquefied is evacuated from the unit H1 via the pipe 7 to introduce it into the unit HF. Thus, the stream of liquefied substrate coming from H1 comprises sugars dissolved in the aqueous phase and the solid material that consists primarily of lignin and rich in cellulose.

Said liquefied substrate simultaneously undergoes, in the reactor of the unit HF, a hydrolysis and a fermentation, a complete hydrolysis so as to solubilize all the sugars that are present in the solid phase. In the reactor of the unit HF, it is possible to add enzymes via the pipe 6b. In addition, in the unit HF, the hydrolyzed substrate is brought into contact with one or more fermentation microorganisms LEV that are introduced via the pipe 9. The microorganisms LEV can be selected from among, for example, the following elements: the yeasts of the genus *Saccharomyces, Saccharomyces cerevisiae, Schizosaccharomyces pombe, Saccharomyces uvarum, Saccharomyces diastaticus, Kluyveromyces fragilis, Candida shehatae, Pichia stipitis, Pachysolen tannophilis*, or the bacteria of the genus *Zymomonas mobilis, Clostridium*, or *Escherichia coli*. In a very preferred manner, a yeast of the type *Saccharomyces*, and even more preferably *Saccharomyces cerevisiae*, is used. Preferably, a yeast that is suitable for producing ethanol, for example yeasts, is used. The fermentable sugars are thus transformed into alcohols and/or solvents by the microorganisms. The stage of hydrolysis and fermentation in the unit HF can be carried out at a temperature of between 30° C. and 35° C. In this unit HF, the fermentation reaction produces a fermentation wine enriched with products of the fermentation reaction, evacuated via the pipe 10, for example alcohols or organic solvents. The fermentation wine also contains solid material that consists primarily of lignin.

Said fermentation wine is introduced into the unit Ex1 to undergo a stage for separation between liquid and solid so as to extract therefrom the solid material, in particular the lignin that has been neither hydrolyzed nor fermented in the units H1 and HF. The extraction of the solid material is carried out in the unit Ex1, which can carry out one of the following techniques: centrifuging, spin-drying or pressing, filtering, decanting. The unit Ex1 produces a stream that is low in solid material evacuated via the pipe 12 and a stream that is enriched with solid material, in particular with lignin, evacuated via the pipe 11.

The stream that is low in solid material is next introduced via the pipe 12 into the separation unit S so as to extract from it the compounds of interest that are evacuated via the pipe 13, for example alcohols or organic solvents. The residues of the separation, commonly called vinasse, are evacuated from the separation unit S via the pipe 14. The vinasse generally consists of water as well as any liquid or solid product that is not converted or not extracted during preceding stages in the units H1, HF, and Ex1. The separation unit S can carry out one or more distillations and optionally a separation of the materials in suspension by, for example, centrifuging, decanting, filtering.

The process that is not in accordance with the invention and that is shown in diagram form by FIG. 1 exhibits the drawback of evacuating a portion of the upgraded compounds, i.e., alcohols or solvents, which remain contained in the solid material, i.e., essentially lignin, evacuated via the pipe 11 during the operation for extraction of the solid material in the unit Ex1. Actually, these alcohols or solvents that are present in liquid form in the fermentation wine circulating in the pipe 10 run the risk of being separated in an imperfect way in stage Ex1 with the tools that are known to one skilled in the art, for example tools for centrifuging, spin-drying, decanting or pressing. At least one fraction of the alcohols or solvents is evacuated via the pipe 11, causing a loss of yield of the process.

Figure 2:
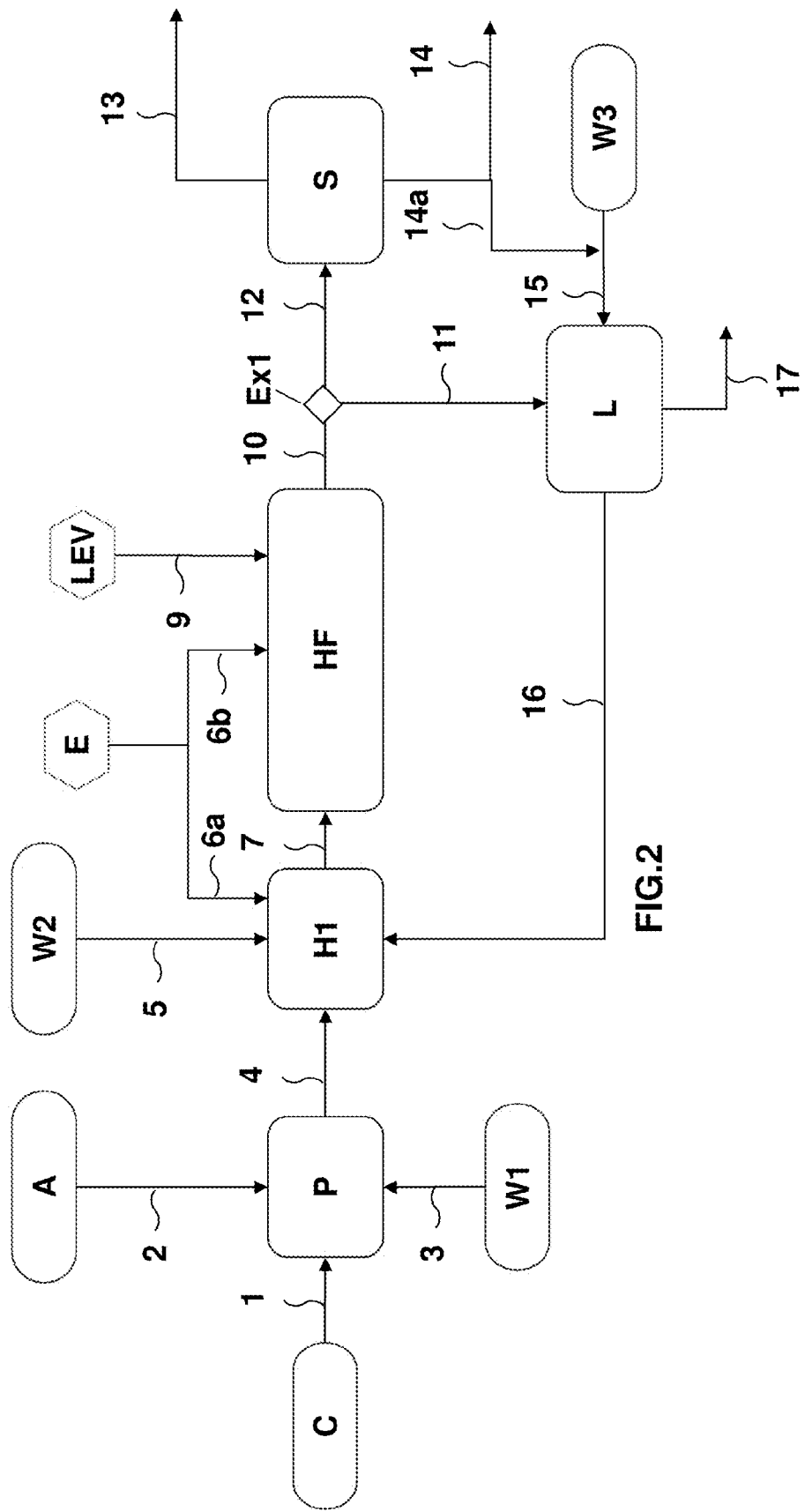
FIG. 2 is a diagrammatic depiction of a first embodiment of the process according to the invention.
Figure 3:
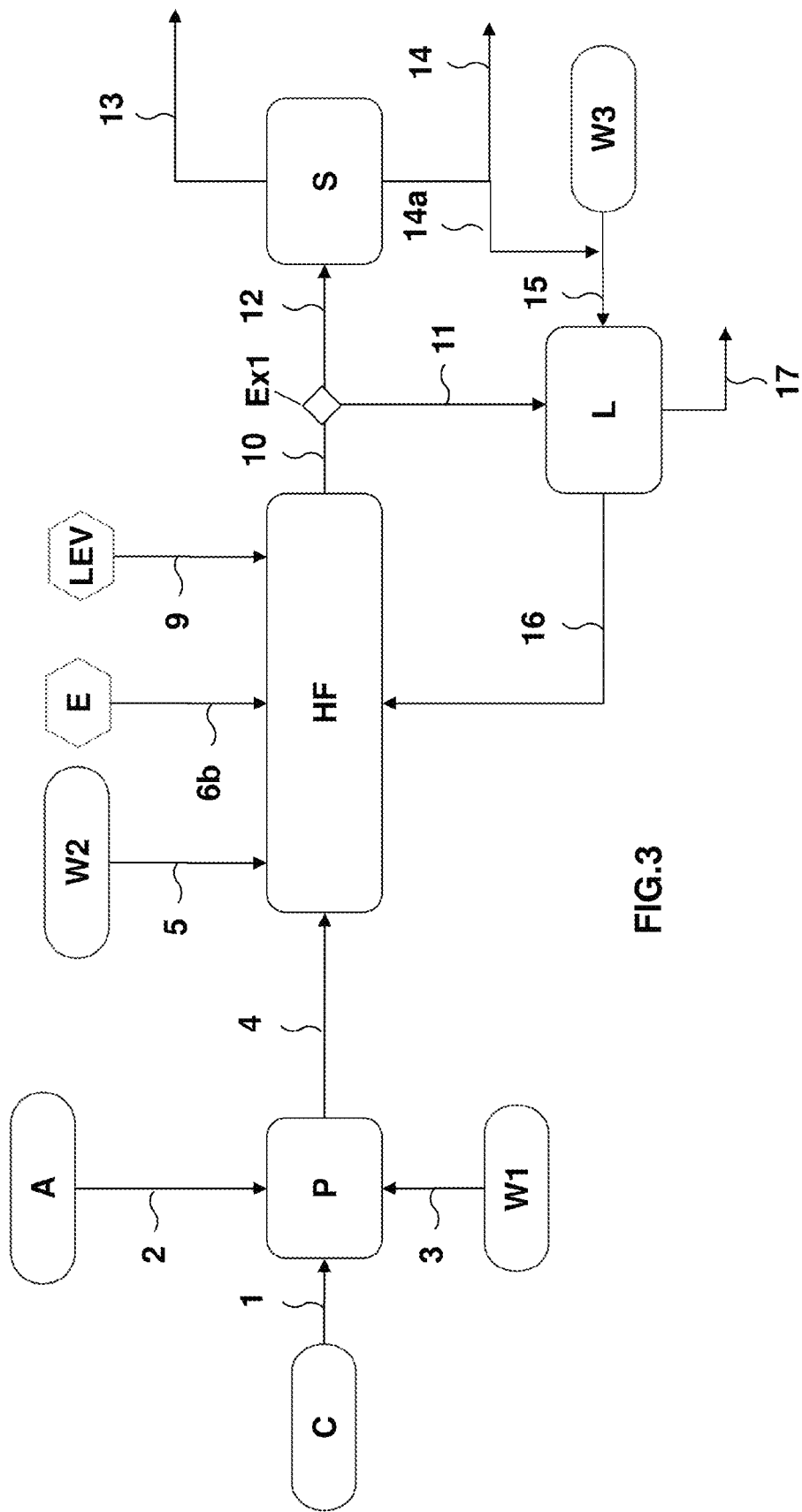
FIG. 3 is a diagrammatic depiction of a second embodiment of the process according to the invention.

The process according to the invention proposes to eliminate this problem of the loss of fermentation products in the solid material by carrying out an operation of washing the solid-material-enriched stream circulating in the pipe 11, making it possible to recycle the fermentation products in the process without providing an additional dilution thereto. The invention will be better understood from reading the description of FIGS. 2 and 3, showing in diagram form two implementations of the process according to the invention. The references of FIG. 2 that are identical to those of FIG. 1 refer to the same elements.

According to the invention, it is possible to carry out the stage for separation of the solid material from the liquid in the unit Ex1 in such a way that the stream 8 that is low in solid contains less than 15% by weight, and preferably less than 10% by weight, and even more preferably less than 5% by weight, of solid materials. The remainder of the stream 8 can consist of sugar dissolved in the aqueous phase. In addition, it is possible to carry out the stage for separation of the solid material from the liquid in the unit Ex1 in such a way that the solid-enriched stream 9 contains between 15% and 55% by weight, and preferably between 20% and 45% by weight, and even more preferably between 25% and 35% by weight, of solid material. Because of the limitations of the equipment for separation between solids and liquids of the unit Ex1, the solid-enriched stream 9 contains at least 45% liquid, which can consist in particular of sugar dissolved in the aqueous phase.

With reference to FIG. 2, a stage for washing the solid material that is contained in the stream coming in via the pipe 11 is carried out in the unit L. In the unit L, a liquid stream is brought in by means of the pipe 15 so as to carry out a washing of the solid material contained in the stream that comes in via the pipe 11. The liquid stream is brought into contact with the solid material, and then the liquid is separated from the solid material. The washing stage in the unit L can be carried out by percolation, by successive operations of liquid/solid mixing and separation, or by any other technique that is known to one skilled in the art. The washing makes it possible to extract via the pipe 16 a liquid stream that is enriched with compounds of interest, i.e., alcohols or solvents, as well as a stream that is low in compounds of interest via the pipe 17. The stream 16 is next recycled in the unit H1 so as to increase the recovery of fermentation products and to increase the overall yield of the process.

With reference to FIG. 2, the liquid stream that is brought in via the pipe 15 can be a stream of fresh water W3 or a portion of the vinasse coming from the unit S brought in via the pipes 14 and then 14a into the unit L. According to the invention, the fact of recycling the stream that is enriched with compounds of interest via the pipe 16 into the unit H1 makes it possible to limit, and even to eliminate, the supply of fresh water W2 directly into the unit H1. For example, the stream 16 represents between 50% by weight and 1,500% by weight, preferably between 100% by weight and 600% by weight, of the flow rate of pretreated substrate introduced via the pipe 4 into the unit H1. Thus, this invention makes it possible to limit, and even to prevent, any additional dilution of the streams in the process linked to the use of water for the washing of the stream 11.

In the process shown in diagram form by FIG. 3, the pretreated substrate that is obtained from the unit P is directly introduced via the pipe 4 and then 7 into the reactor of the unit HF for simultaneous hydrolysis and fermentation. The water W2, the enzymes E, and the yeasts LEV are introduced into the reactor of the unit HF respectively via the pipes 5, 6b, and 9. In this case, the stream 16 that is enriched with the compound of interest is introduced into the reactor of the unit HF.

EXAMPLES

The examples below illustrate the invention, without limiting its scope.

Example 1

According to the Process of FIG. 1 (not in Accordance with the Invention)

In this example, a process for the production of ethanol from straw with the following characteristics is presented:

Feedstock: Wheat straw, flow rate 89.60 tons/hour, mean composition:

|  | % (Dry Base) |
|---|---|
| Cellulose | 39.1% |
| Hemicellulose | 26.9% |
| Lignin | 17.9% |
| Others (Ashes, Extractibles, etc.) | 16.1% |

Preparation of the Feedstock and Pretreatment in the Unit P:

The straw is ground on a 50-mm grid and then impregnated with the acid $H_2SO_4$, diluted to 0.7 g/liter. The impregnation is followed by a solid/liquid separation, and the impregnation liquor is recycled; the dry material (MS) of the solid entering pretreatment is 45% by weight. The pretreatment by vapor explosion is carried out at 200° C. in a continuous configuration employing a short dwell time. The medium is abruptly expanded to a pressure of 1.3 atm. The pretreated substrate is sent to the enzymatic hydrolysis reactor H1.

Enzymatic Hydrolysis and Conversion into Ethanol:

The concentration of solids at the inlet of the liquefaction reactor in the unit H1 is 14% by weight. To reach this dilution level, 114.3 tons/hour of the process water W2 is mixed with the pretreated substrate. After 10 hours of operation, the liquefied mixture is sent into the unit HF, which operates in SSF mode. In this stage, the enzymes continue to act on the cellulose at the same time that the fermentation microorganism (Saccharomyces cerevisiae) acts on the released sugars. The overall yield of the conversion of cellulose into ethanol is 0.40 g of ethanol per g of cellulose that is introduced. The pentoses that are present are not converted by the selected fermentation microorganism. The ethanol titer of the stream sent to separation is 39.4 g of ethanol/kg of wine.

Separation:

The wine that is obtained from the unit HF is sent into a decanter in the unit Ex1, where the solid material, in particular the lignin, is separated from the wine before the stage for recovery of the ethanol in the separation unit S. In this separation stage, a stream that contains 31.3% of solid material is produced. Given the nature of the separation, this stream also contains a large quantity of fermentation products, in particular ethanol, trapped. The loss of ethanol during this stage is estimated at 20.7%.

Recovery of Ethanol:

The separation in the unit S is done by distillation. The extraction yield is 99.6%. Thus, the process makes it possible to produce annually 74,890 tons of ethanol, and it has a specific consumption of process water of 12.2 tons of water/ton of ethanol that is produced.

Example 2

According to the Process of FIG. 1 (not in Accordance with the Invention)

In this example, a process for the production of ethanol from straw with the following characteristics is presented:

Feedstock: Wheat straw, flow rate 89.60 tons/hour, mean composition:

|  | % (MS Base) |
|---|---|
| Cellulose | 39.1% |
| Hemicellulose | 26.9% |
| Lignin | 17.9% |
| Others (Ashes, Extractibles, etc.) | 16.1% |

Preparation of the Feedstock and Pretreatment in the Unit P:

The straw is ground on a 50-mm grid and then impregnated with the acid $H_2SO_4$, diluted to 0.7 g/liter. The impregnation is followed by a solid/liquid separation, and the impregnation liquor is recycled; the dry material (MS) of the solid entering pretreatment is 45% by weight. The pretreatment by vapor explosion is carried out at 200° C. in a continuous configuration employing a short dwell time. The medium is abruptly expanded to a pressure of 1.3 atm. The pretreated substrate is sent to the enzymatic hydrolysis reactor H1.

Enzymatic Hydrolysis and Conversion into Ethanol:

The concentration of solids at the inlet of the liquefaction reactor in the unit H1 is 14%. To reach this dilution level, 114.3 tons/hour of process water W2 is mixed with the pretreated substrate. After 10 hours of operation, the liquefied mixture is sent into the unit HF, which operates in SSF mode. In this stage, the enzymes continue to act on the cellulose at the same time that the fermentation microorganism (Saccharomyces cerevisiae) acts on the released sugars. The overall yield of the conversion of cellulose into ethanol is 0.40 g of ethanol per g of cellulose that is introduced. The pentoses that are present are not converted by the selected fermentation microorganism. The ethanol titer of the stream sent to separation is 39.4 g of ethanol/kg of wine.

Separation:

The wine that is obtained from the unit HF is sent into a decanter in the unit Ex1, where the solid material, in particular the lignin, is separated from the wine before the stage for recovery of the ethanol in the separation unit S. In this separation stage, a stream that contains 30.8% of solid material is produced.

Washing the Stream of Solid Material:

Given the nature of the separation, approximately 20% of the ethanol remains trapped in the solid material. A countercurrent washing of the solid material is then carried out for the purpose of reducing losses. 115 tons/hour of process water is used in this operation. The ethanol losses drop to 1.4%. The dilute wine that is recovered contains 20.1 g of ethanol/kg of wine and is mixed with clarified wine that is obtained before being sent to the separation unit S.

Recovery of Ethanol:

The clarified wine that is mixed with dilute wine obtained from washing is sent to the distillation columns of the unit S. Due to the low concentration of ethanol of the dilute wine obtained from washing, the total wine contains only 35.2 g of ethanol per kg of wine entering the distillation stage, value 10.7% less than that obtained at the end of SSF fermentation.

The separation in the unit S is done by distillation. The extraction yield is 99.6%. Thus, the process makes it possible to produce annually 93,087 tons of ethanol, and it has a specific consumption of process water of 19.6 tons of water/ton of ethanol that is produced.

Example 3

According to the Process of FIG. 2 (in Accordance with the Invention)

In this example, a process for the production of ethanol from straw with the following characteristics is presented:

Feedstock: Wheat straw, flow rate 89.60 tons/hour, mean composition:

|  | % (Dry Base) |
| --- | --- |
| Cellulose | 39.1% |
| Hemicellulose | 26.9% |
| Lignin | 17.9% |
| Others (Ashes, Extractibles, etc.) | 16.1% |

Preparation of the Feedstock and Pretreatment in the Unit P:

The straw is ground on a 50-mm grid and then impregnated with the acid $H_2SO_4$, diluted to 0.7 g/liter. The impregnation is followed by a solid/liquid separation, and the impregnation liquor is recycled; the dry material (MS) of the solid entering pretreatment is 45% by weight. The pretreatment by vapor explosion is carried out at 200° C. in a continuous configuration employing a short dwell time. The medium is abruptly expanded to a pressure of 1.3 atm. The pretreated substrate is sent to the enzymatic hydrolysis reactor H1.

Enzymatic Hydrolysis and Conversion into Ethanol:

The concentration of solids at the inlet of the liquefaction reactor in the unit H1 is 14% by weight. To reach this dilution level, 114.3 tons/hour of the dilution water that comes in via the pipe 16 is mixed with the pretreated substrate. This dilution water contains 25.0 g of ethanol/kg of solution originating from the recycling of the water that is used for washing the stream of solids obtained at the end of the liquid/solid separation operation Ex1 leaving the unit HF.

After 10 hours of operation, the liquefied mixture is sent into the unit HF, which operates in SSF mode. In this stage, the enzymes continue to act on the cellulose at the same time that the fermentation microorganism (*Saccharomyces cerevisiae*) acts on the released sugars. The overall yield of the conversion of cellulose into ethanol is 0.40 g of ethanol per g of cellulose that is introduced. The pentoses that are present are not converted by the selected fermentation microorganism. The ethanol titer of the stream sent to separation is 48.9 g of ethanol/kg of wine.

Separation:

The wine that is obtained from the unit HF is sent to a decanter in the unit Ex1, where the solid material, in particular the lignin, is separated from the wine before the stage for recovery of the ethanol in the separation unit S. In this separation stage, a stream that contains 30.7% by weight of solid material is produced.

Washing the Stream of Solid Material:

So as to recover the ethanol that is trapped in the solid material, a stage for washing the solid material is carried out. In this example, all of the water that is sent as dilution water to the enzymatic hydrolysis stage is first used to wash the solid material in the counter-current washing unit L in three contact stages. Then, the washing water is introduced into the unit H1. The ethanol losses are then reduced by 93.2% relative to the results of Example 1, or 1.4% overall loss.

Recovery of Ethanol:

The separation in the unit S is done by distillation. The extraction yield is 99.6%. Thus, the process makes it possible to produce annually 92,607 tons of ethanol, and it has a specific consumption of process water of 9.9 tons of water/ton of ethanol that is produced, or 18.8% and 49.5% of reduction relative to the consumption of water in Examples 1 and 2, respectively.

Example 4

According to the Process of FIG. 1 (not in Accordance with the Invention)

In this example, a process for the production of ethanol from straw with the following characteristics is presented:

Feedstock: Wheat straw, flow rate 89.60 tons/hour, mean composition:

|  | % (Dry Base) |
| --- | --- |
| Cellulose | 39.1% |
| Hemicellulose | 26.9% |
| Lignin | 17.9% |
| Others (Ashes, Extractibles, etc.) | 16.1% |

Preparation of the Feedstock and Pretreatment in the Unit P:

The straw is ground on a 50-mm grid and then impregnated with the acid $H_2SO_4$, diluted to 0.7 g/liter. The impregnation is followed by a solid/liquid separation, and the impregnation liquor is recycled; the dry material (MS) of the solid entering the pretreatment is 45% by weight. The pretreatment by vapor explosion is carried out at 200° C. in a continuous configuration employing a short dwell time. The medium is abruptly expanded to a pressure of 1.3 atm. The pretreated substrate is sent to the enzymatic hydrolysis reactor H1.

Enzymatic Hydrolysis and Conversion into Ethanol:

The concentration of solids at the inlet of the liquefaction reactor in the unit H1 is 14% by weight. To reach this dilution level, 114.3 tons/hour of process water W2 is mixed with the pretreated substrate. After 10 hours of operation, the liquefied mixture is sent into the unit HF, which operates in SSF mode. In this stage, the enzymes continue to act on the cellulose at the same time that the fermentation microorganism (*Saccharomyces cerevisiae* that comes from a modified strain that is able to carry out the co-fermentation of hexoses and pentoses) acts on the pentoses that are present and the released hexoses. The overall yield of the conversion of cellulose into ethanol is 0.39 g of ethanol per g of cellulose that is introduced. The conversion of pentoses into ethanol rises to 0.11 g of ethanol per g of pentose that is introduced. The ethanol titer of the stream sent to separation is 47.5 g of ethanol/kg of wine.

Separation:

The wine that is obtained from the unit HF is sent to a decanter in the unit Ex1, where the solid material, in particular the lignin, is separated from the wine before the stage for recovery of the ethanol in the separation unit S. In this separation stage, a stream that contains 31.5% by weight of solid material is produced. Given the nature of the separation, this stream also contains a large quantity of fermentation products, in particular ethanol, trapped. The loss of ethanol during this stage is estimated at 20.7%.

Recovery of Ethanol:

The separation in the unit S is done by distillation. The extraction yield is 99.6%. Thus, the process makes it possible to produce annually 89,707 tons of ethanol, and it has a specific consumption of process water of 10.2 tons of water/ton of ethanol.

Example 5

According to the Process of FIG. 2 (in Accordance with the Invention)

In this example, a process for the production of ethanol from straw with the following characteristics is presented:

Feedstock: Wheat straw, flow rate 89.60 tons/hour, mean composition:

|  | % (Dry Base) |
| --- | --- |
| Cellulose | 39.1% |
| Hemicellulose | 26.9% |
| Lignin | 17.9% |
| Others (Ashes, Extractibles, etc.) | 16.1% |

Preparation of the Feedstock and Pretreatment in the Unit P:

The straw is ground on a 50-mm grid and then impregnated with the acid $H_2SO_4$, diluted to 0.7 g/liter. The impregnation is followed by a solid/liquid separation, and the impregnation liquor is recycled; the dry material (MS) of the solid entering pretreatment is 45% by weight. The pretreatment by vapor explosion is carried out at 200° C. in a continuous configuration employing a short dwell time. The medium is abruptly expanded to a pressure of 1.3 atm. The pretreated substrate is sent to the enzymatic hydrolysis reactor H1.

Enzymatic Hydrolysis and Conversion into Ethanol:

The concentration of solids at the inlet of the liquefaction reactor in the unit H1 is 14% by weight. To reach this dilution level, 114.3 tons/hour of dilution water is mixed with the pretreated substrate. This dilution water contains 31.1 g of ethanol/kg of solution and 101.7 g of pentoses/kg of solution originating from the recycling of the vinasse produced by distillation and used for washing the stream of solid material obtained at the end of the liquid/solid separation operation Ex1 leaving the reactor HF.

After 10 hours of operation, the liquefied mixture is sent into the unit HF, which operates in SSF mode. In this stage, the enzymes continue to act on the cellulose at the same time that the fermentation microorganism (*Saccharomyces cerevisiae* that is obtained from a modified strain that is able to carry out the co-fermentation of hexoses and pentoses) acts on the released sugars. The overall yield of the conversion of cellulose into ethanol is 0.35 g of ethanol per g of cellulose that is introduced. The conversion of pentoses into ethanol rises to 0.11 g of ethanol per g of pentose that is introduced. The drop in yield is explained by the highest concentration of sugars and ethanol in the enzymatic hydrolysis stage. The ethanol titer of the stream sent to separation is 61.0 g of ethanol/kg of wine.

Separation:

The wine that is obtained from the units HF is sent to a decanter in the unit Ex1, where the solid material, in particular the lignin, is separated from the wine before the stage for recovery of the ethanol in the separation unit S. In this separation stage, a stream that contains 32.3% of solid material is produced.

Washing the Stream of Solid Material:

So as to recover the ethanol that is trapped in the solid material, a stage for washing the solid material is carried out. In this example, all of the water that is sent as dilution water to the enzymatic hydrolysis stage in the unit H1 comes from vinasse produced by distillation in the unit S. This vinasse is first used to wash the solid material in the counter-current washing unit L in three contact stages. Then, the vinasse that is obtained from the unit L is introduced into the unit H1. The ethanol losses are then reduced by 92.7% relative to the results of Example 4, or 1.5% overall loss.

Recovery of Ethanol:

The separation in the unit S is done by distillation. The extraction yield is 99.6%. Thus, the process makes it possible to produce annually 114,051 tons of ethanol, and it has a specific consumption of process water of 0.0 ton of water/ton of ethanol produced in a continuous mode.

The invention claimed is:

1. Process for the production of alcohol and/or solvent from a biomass feedstock, in which the following stages are carried out:
   a) a pretreatment stage is carried out by heating and bringing the biomass feedstock into contact with water and an acid or base compound in such a way as to obtain a pretreated substrate,
   b) bringing the pretreated substrate into contact with cellulase enzymes and with a liquid stream enriched with fermentation products and obtained in stage e) in such a way as to obtain a hydrolyzate comprising a solid residue and a liquid phase containing sugars, wherein the liquid stream that is enriched with fermentation products has a flow rate of between 50% and 1,500% by weight of the flow rate of pretreated substrate,
   c) conducting alcoholic fermentation of the hydrolyzate by means of an alcohologenic microorganism in such a way as to produce a fermentation wine comprising a solid material and a liquid phase containing fermentation products,
   d) extracting at least a portion of the solid material contained in the fermentation wine in such a way as to obtain a stream that is enriched with solid material and a fermentation wine that is low in solid material,
   e) washing the stream that is enriched with solid material with a liquid stream in such a way as to obtain said liquid stream that is enriched with fermentation products, with the liquid stream that is enriched with fermentation products being recycled to stage b), and
   f) separating the fermentation wine that is low in solid material in such a way as to obtain at least one purified stream comprising an alcohol or a solvent and at least one vinasse stream,
   wherein the liquid stream used in stage e) comprises at least a portion of the vinasse stream obtained in stage f).

2. Process according to claim 1, in which the liquid stream from stage e) consists of fresh water.

3. Process according to claim 1, in which in stage e), the stream that is enriched with solid material is brought into contact with said liquid stream, and then the liquid stream is separated from the solid material.

4. Process according to claim 1, in which stage d) is carried out in such a way that said stream that is enriched with solid material comprises between 15% by weight and 55% by weight of solid material and in such a way that said fermentation wine that is low in solid material comprises less than 15% by weight of solid material.

5. Process according to claim 1, in which stage b) is carried out in a first reactor, and stage c) is carried out in a second reactor that is separate from the first reactor.

6. Process according to claim 1, in which stage b) and stage c) are carried out simultaneously in the same reactor.

7. Process according to claim 1, in which the cellulase enzymes are produced by a microorganism that is selected from among the mushrooms that belong to the genera *Trichoderma, Aspergillus, Penicillium*, or *Schizophyllum*, or the anaerobic bacteria that belong to the genus *Clostridium*.

8. Process according to claim 1, in which the alcohologenic microorganism is selected from among the microorganisms of the genus *Saccharomyces, Saccharomyces cerevisiae, Schizosaccharomyces pombe, Saccharomyces uvarum, Saccharomyces diastaticus, Kluyveromyces fragilis, Candida shehatae, Pichia stipitis, Pachysolen tannophilis, Zymomonas mobilis, Clostridium*, and *Escherichia coli*.

9. Process according to claim 1, in which the biomass feedstock consists of at least one of the following elements: wood, cultivated plants, agricultural lignocellulosic waste, and residues of the industry for transformation of the lignocellulosic materials.

10. Process according to claim 1, in which in stage a), a vapor explosion of the biomass is carried out by exerting compression and then carrying out pressure relief of the biomass mixed with water and an acid compound.

11. Process according to claim 1, in which in stage c), an alcohologenic organism that produces at least ethanol is used.

\* \* \* \* \*